US012805814B2

(12) United States Patent
Tsukagoshi

(10) Patent No.: US 12,805,814 B2
(45) Date of Patent: Nov. 24, 2026

(54) X-RAY COMPUTED TOMOGRAPHY APPARATUS

(71) Applicant: Canon Kabushiki Kaisha, Tokyo (JP)

(72) Inventor: Shinsuke Tsukagoshi, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 171 days.

(21) Appl. No.: 18/973,208

(22) Filed: Dec. 9, 2024

(65) Prior Publication Data

US 2025/0186006 A1 Jun. 12, 2025

(30) Foreign Application Priority Data

Dec. 12, 2023 (JP) ................................. 2023-209482

(51) Int. Cl.
*A61B 6/03* (2006.01)
*A61B 6/00* (2006.01)

(52) U.S. Cl.
CPC .............. *A61B 6/03* (2013.01); *A61B 6/4447* (2013.01)

(58) Field of Classification Search
CPC ......... A61B 6/03; A61B 6/4447; A61B 6/482; A61B 6/4241; A61B 6/488; A61B 6/542; A61B 6/032
See application file for complete search history.

(56) References Cited

U.S. PATENT DOCUMENTS 9,888,901 B2 * 2/2018 Iwai ....................... A61B 6/032

FOREIGN PATENT DOCUMENTS

JP 2017-217460 A 12/2017
JP 2021-142128 A 9/2021

* cited by examiner

*Primary Examiner* — Jurie Yun

(74) *Attorney, Agent, or Firm* — Oblon, McClelland, Maier & Neustadt, L.L.P.

(57) ABSTRACT

According to one embodiment, an X-ray computed tomography apparatus includes a gantry and a processing circuitry. The processing circuitry acquires a first image in which a region of interest present on a subject is included, the first image being collected by a first scan of the subject; sets a specific region including the region of interest with respect to the first image; determines a scan condition for a photon counting CT scan as a second scan based on the specific region, the scan condition including an X-ray dose and/or an energy bin conforming to an image quality standard of the region of interest; and controls the gantry according to the scan condition to executes the second scan on the subject.

13 Claims, 9 Drawing Sheets

X-RAY COMPUTED TOMOGRAPHY APPARATUS

CROSS-REFERENCE TO RELATED APPLICATION

This application is based upon and claims the benefit of priority from Japanese Patent Application No. 2023-209482, filed Dec. 12, 2023, the entire contents of which are incorporated herein by reference.

FIELD

Embodiments described herein relate generally to an X-ray computed tomography apparatus.

BACKGROUND

For example, in cancer treatment, follow-up imaging is performed to confirm a therapeutic effect by comparing a CT image after treatment with a CT image before treatment. In the CT scan performed after the treatment, an X-ray dose is determined in consideration of not only the image quality of the region where the cancer is present but also the image quality of the region other than the region where the cancer is present using auto exposure control (AEC) even in a case where the treatment effect for the cancer at a specific position is observed.

DETAILED DESCRIPTION

In general, according to one embodiment, an X-ray computed tomography apparatus includes a gantry, an acquisition unit, a setting unit, a determination unit, and a scan control unit. The gantry includes an X-ray tube that generates an X-ray, a high-voltage device that applies a high voltage to the X-ray tube, an X-ray detector that detects the X-ray generated from the X-ray tube, and a data acquisition system that collects count data of the X-ray detected by the X-ray detector for each energy bin. The acquisition unit acquires a first image collected by a first scan of a subject. A region of interest present on the subject is included in the first image. The setting unit sets a specific region including the region of interest with respect to the first image. The determination unit determines a scan condition of a photon-counting CT scan which is a second scan based on the specific region, and the scan condition includes an X-ray dose and/or an energy bin conforming to image quality standards of the region of interest. The scan control unit controls the gantry according to the scan condition and executes a second scan on the subject.

Hereinafter, the X-ray computed tomography apparatus according to the present embodiment will be described in detail with reference to the drawings.

The X-ray computed tomography apparatus according to the present embodiment includes various types such as a third generation CT and a fourth generation CT, and any type is applicable to the present embodiment. Here, the third generation CT is a Rotate/Rotate-Type in which the X-ray tube and the X-ray detector integrally rotate around the subject. The fourth generation CT is a Stationary/Rotate-Type in which a large number of X-ray detection elements arranged in a ring shape are fixed, and only an X-ray tube rotates around a subject. In addition, the X-ray computed tomography apparatus according to the present embodiment can be applied to a single tube type in which one pair of an X-ray tube and an X-ray detector is mounted on a rotation ring, or a multi-tube type in which a plurality of pairs of an X-ray tube and an X-ray detector are mounted on a rotation ring. However, in the following description, the X-ray computed tomography apparatus is assumed to be a single tube type.

The X-ray computed tomography apparatus according to the present embodiment is assumed to be a photon-counting CT apparatus that performs photon-counting computed tomography (PCCT).

Figure 1:
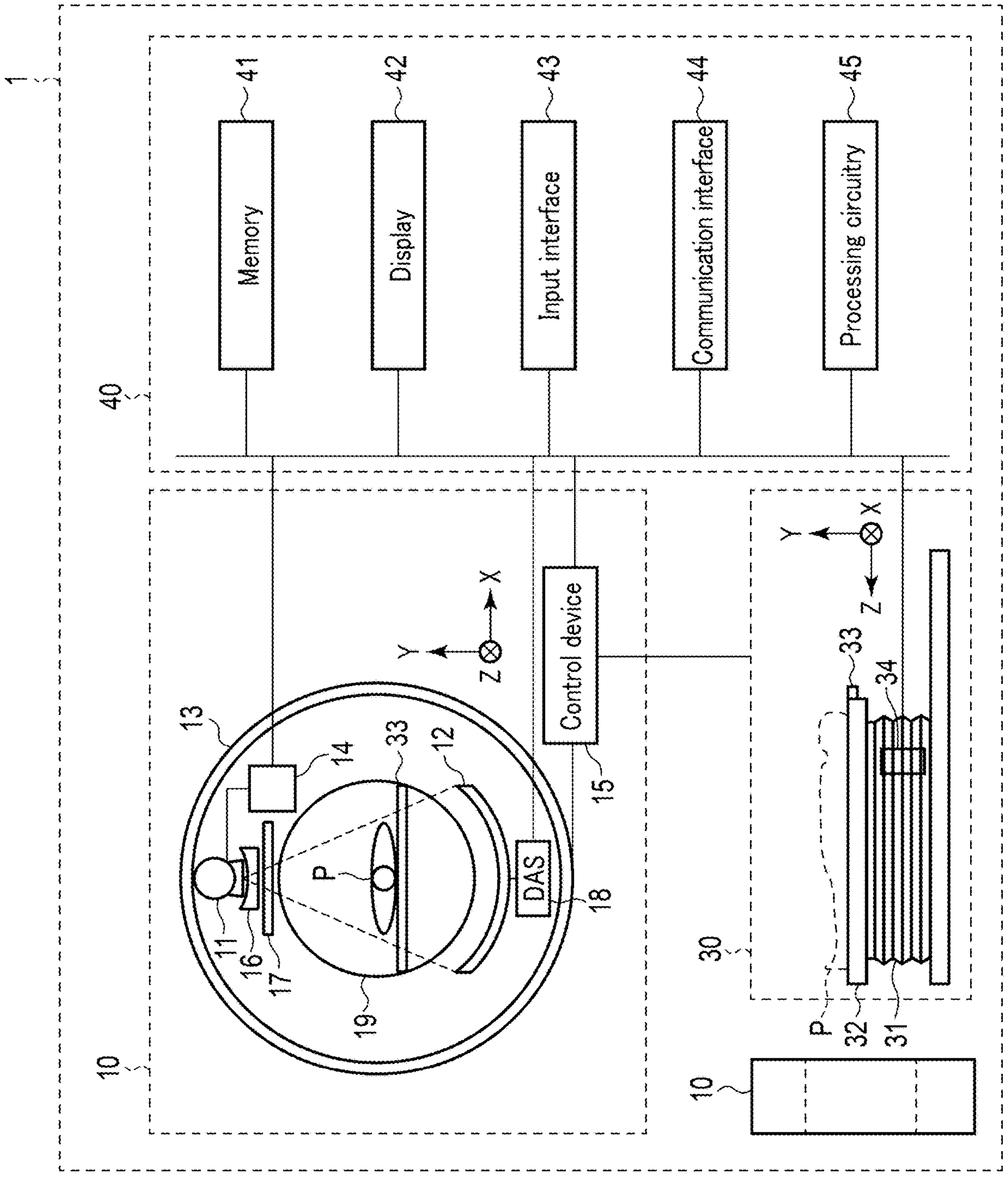
FIG. 1 is a diagram showing a configuration of an X-ray computed tomography apparatus according to the present embodiment.

FIG. 1 is a diagram showing a configuration of an X-ray computed tomography apparatus 1 according to the present embodiment. As shown in FIG. 1, the X-ray computed tomography apparatus 1 includes a gantry 10, a couch 30, and a console 40. Note that, in FIG. 1, the gantry 10 is shown at a plurality of locations for convenience of description, but one stand 10 or a plurality of stands may be mounted on the X-ray computed tomography apparatus 1. The gantry 10 is a scanning device having a configuration for PCCT scanning of a subject P. The couch 30 is a transfer device for placing the subject P to be subjected to the X-ray CT imaging and positioning the subject P. The console 40 is a computer that controls the gantry 10. For example, the gantry 10 and the couch 30 are installed in a CT inspection room, and the console 40 is installed in a control room adjacent to the CT inspection room. The gantry 10, the couch 30, and the console 40 are connected in a wired or wireless manner so as to be able to communicate with each other. The console 40 is not necessarily installed in the control room. For example, the console 40 may be installed in the same room together with the gantry 10 and the couch 30. The console 40 may also be incorporated into the gantry 10.

As shown in FIG. 1, the gantry 10 includes an X-ray tube 11, an X-ray detector 12, a rotary frame 13, an X-ray high-voltage device 14, a control device 15, a wedge 16, a collimator 17, and a data acquisition system (DAS) 18.

The X-ray tube 11 generates X-rays.

Specifically, the X-ray tube 11 includes a cathode that generates thermoelectrons, an anode that receives the thermoelectrons flying from the cathode and generates X-rays, and a vacuum tube that holds the cathode and the anode. The X-ray tube 11 is connected to the X-ray high-voltage device 14 through a high voltage cable. A tube voltage is applied between the cathode and the anode by the X-ray high-voltage device 14. The application of the tube voltage causes thermoelectrons to fly from the cathode toward the anode. If thermoelectrons fly from the cathode toward the anode, a tube current flows. By application of a high voltage and supply of a filament current from the X-ray high-voltage device 14, thermoelectrons fly from the cathode (filament) toward the anode (target), and the thermoelectrons collide with the anode, thereby generating X-rays. For example, the X-ray tube 11 is a rotating anode type X-ray tube that generates X-rays by irradiating a rotating anode with thermoelectrons.

The X-ray detector 12 detects the X-rays generated from the X-ray tube 11 and passing through the subject P, and outputs an electric signal corresponding to the energy of the detected X-rays to the data acquisition system 18. The X-ray detector 12 has a structure in which a plurality of X-ray detection element arrays in which a plurality of X-ray detection elements are arrayed in the channel direction are arrayed in the slice direction (column direction). The X-ray detector 12 is, for example, an indirect conversion type detector having a grid, a scintillator array, and an optical sensor array. The scintillator array includes a plurality of scintillators. Each scintillator generates a plurality of fluorescent photons according to the energy of incident X-ray photons. The grid includes an X-ray shielding plate that is disposed on the X-ray incident surface side of the scintillator array and absorbs scattered X-rays. Note that the grid may also be referred to as a collimator (a one-dimensional collimator or two-dimensional collimator). The optical sensor array converts the plurality of fluorescent photons from the scintillator into an electrical signal having a peak value corresponding to the energy of the incident X-ray photons. As the optical sensor, for example, a photodiode is used.

The X-ray detector 12 may be a direct-conversion type detector. As the direct detection type X-ray detector 12, for example, a type including a semiconductor diode in which electrodes are attached to both ends of a semiconductor is applicable. The X-ray photons incident on the semiconductor are converted into electron-hole pairs. The number of electron-hole pairs generated by the incidence of one X-ray photon depends on the energy of the incident X-ray photon. The electrons and the holes are attracted to each other by a pair of electrodes formed at both ends of the semiconductor. The pair of electrons generate electrical signals having a peak value corresponding to the charge of the electron-hole pairs. One electrical signal includes a peak value corresponding to the energy of the incident X-ray photon.

The rotary frame 13 is an annular frame that rotatably supports the X-ray tube 11 and the X-ray detector 12 about a rotation axis (Z axis). Specifically, the rotary frame 13 supports the X-ray tube 11 and the X-ray detector 12 facing each other. The rotary frame 13 is supported by a fixed frame (not shown) so as to be rotatable about a rotation axis. The control device 15 rotates the rotary frame 13 about the rotation axis to rotate the X-ray tube 11 and the X-ray detector 12 about the rotation axis. The rotary frame 13 receives power from the drive mechanism of the control device 15 and rotates around the rotation axis at a constant angular velocity. An image field of view (FOV) is set in an opening 19 of the rotary frame 13.

In the present embodiment, the longitudinal direction of the rotation axis of the rotary frame 13 or a top plate 33 of the couch 30 in the non-tilting state is defined as the Z-axis direction, the axial direction orthogonal to the Z-axis direction and horizontal to the floor surface is defined as the X-axis direction, and the axial direction orthogonal to the Z-axis direction and vertical to the floor surface is defined as the Y-axis direction.

The X-ray high-voltage device 14 includes a high-voltage generator and an X-ray controller. The high voltage generator includes an electrical circuit such as a transformer and a rectifier, and generates a high voltage to be applied to the X-ray tube 11 and a filament current to be supplied to the X-ray tube 11. The X-ray control device controls an output voltage according to the X-rays emitted from the X-ray tube 11. The high-voltage generator may be a transformer type or an inverter type. The X-ray high-voltage device 14 may be provided in the rotary frame 13 in the gantry 10, or may be provided in a fixed frame (not shown) in the gantry 10.

The wedge 16 adjusts the dose of the X-rays with which the subject P is irradiated. Specifically, the wedge 16 attenuates the X-rays so that the dose of the X-rays emitted from the X-ray tube 11 to the subject P have a predetermined distribution. For example, a metal plate made of aluminum or the like such as a wedge filter or a bow-tie filter is used as the wedge 16.

The collimator 17 limits an irradiation range of the X-rays transmitted through the wedge 16. The collimator 17 slidably supports a plurality of lead plates that shield X-rays, and adjusts a form of a slit formed by the plurality of lead plates. The collimator 17 may also be referred to as an X-ray aperture.

The data acquisition system 18 collects count data of X-rays detected by the X-ray detector 12 for each energy bin. As an example, the data acquisition system 18 includes a pre-amplifier, a waveform shaping circuit, a pulse-height discriminator circuit, and a counting circuit. The pre-amplifier amplifies an electric signal having a peak value corresponding to the energy of the X-ray photon detected by the X-ray detector 12 at a predetermined magnification. The waveform shaping circuit shapes the waveform of the electrical signal output by the pre-amplifier. The pulse-height discriminator applies an energy threshold corresponding to each of the plurality of energy bins to the electrical signal output by the waveform shaping circuit, and outputs an electrical pulse signal corresponding to the energy bin to which the electrical signal belongs. The counting circuit counts the electrical pulse signal output from the pulse-height discriminator in units of view periods for each energy bin, thereby generating count data representing the number of the count of X-ray photons for each energy bin. The data acquisition system 18 is implemented by, for example, an application specific integrated circuit (ASIC). The count data is transmitted to the console 40 via a non-contact data transmission device or the like.

The control device 15 controls the X-ray high-voltage device 14 and the data acquisition system 18 to perform a PCCT scan according to the control of a processing circuitry 45 of the console 40. The control device 15 includes a processing circuitry including a central processing unit (CPU), a micro processing unit (MPU), or the like, and a drive mechanism such as a motor and an actuator. The processing circuitry includes a processor such as a CPU and a memory such as a read only memory (ROM) and a random access memory (RAM) as hardware resources. Furthermore, the control device 15 may be implemented by an ASIC or a field programmable gate array (FPGA). Furthermore, the control device 15 may be implemented by another complex programmable logic device (CPLD) or a simple programmable logic device (SPLD). The control device 15 has a function of controlling the operation of the gantry 10 and the couch 30 in response to an input signal from an input interface 43 (described later) attached to the console 40 or the gantry 10. For example, the control device 15 performs control to rotate the rotary frame 13 in response to an input signal, control to tilt the gantry 10, and control to operate the couch 30 and the top plate 33. Note that the control of tilting the gantry 10 is implemented by the control device 15 rotating the rotary frame 13 about an axis parallel to the X-axis direction based on the inclination angle (tilt angle) information input by the input interface attached to the gantry 10. Note that the control device 15 may be provided on the gantry 10 or may be provided on the console 40.

The couch 30 includes a base 31, a support frame 32, a top plate 33, and a couch driving device 34. The base 31 is installed on a floor surface. The base 31 is a housing that supports the support frame 32 so as to be movable in a direction perpendicular to the floor surface (Y-axis direction). The support frame 32 is a frame provided above the base 31. The support frame 32 slidably supports the top plate 33 along the rotation axis (Z axis). The top plate 33 is a flexible plate on which the subject P is placed.

The couch driving device 34 is accommodated in a housing of the couch 30. The couch driving device 34 is a motor or an actuator that generates power for moving the support frame 32 and the top plate 33 on which the subject P is placed. The couch driving device 34 operates according to control by the console 40 or the like.

The console 40 includes a memory 41, a display 42, an input interface 43, a communication interface 44, and a processing circuitry 45. Data communication among the memory 41, the display 42, the input interface 43, the communication interface 44, and the processing circuitry 45 is performed via a bus (BUS). Although the console 40 will be described as a separate body from the gantry 10, the gantry 10 may include the console 40 or a part of each component of the console 40.

The memory 41 is a storage device such as a hard disk drive (HDD), a solid state drive (SSD), or an integrated circuit storage device that stores various types of information. The memory 41 stores, for example, count data and reconstructed image data. The memory 41 may be a portable storage medium such as a compact disc (CD), a digital versatile disc (DVD), or a flash memory, in addition to an HDD, an SSD, or the like. The memory 41 may be a drive device that reads and writes various types of information from and to a semiconductor memory element such as a flash memory or a random access memory (RAM). In addition, the storage area of the memory 41 may be in the X-ray computed tomography apparatus 1 or in an external storage device connected via a network. The memory 41 stores a database to be described later.

The display 42 displays various types of information. For example, the display 42 outputs the CT image generated by the processing circuitry 45, a graphical user interface (GUI) for receiving various operations from the operator, and the like. As the display 42, any of various types of displays can be used as appropriate. For example, a liquid crystal display (LCD), a cathode ray tube (CRT) display, an organic electroluminescence (OELD) display, or a plasma display can be used as the display 42. Furthermore, the display 42 may be provided on the gantry 10. In addition, the display 42 may be a desktop type or may be configured by a tablet terminal or the like capable of wirelessly communicating with the main body of the console 40.

The input interface 43 receives various input operations from an operator, converts the received input operations into electrical signals, and outputs the electrical signals to the processing circuitry 45. For example, the input interface 43 receives, from the operator, a collection condition for collecting count data, a reconstruction condition for reconstructing a PCCT image, an image processing condition for generating a post-processing image from a PCCT image, and the like. As the input interface 43, for example, a mouse, a keyboard, a trackball, a switch, a button, a joystick, a touch pad, a touch panel display, and the like can be appropriately used. Note that, in the present embodiment, the input interface 43 is not limited to one including physical operation components such as a mouse, a keyboard, a trackball, a switch, a button, a joystick, a touch pad, and a touch panel display. For example, an electric signal processing circuitry that receives an electric signal corresponding to an input operation from an external input device provided separately from the device and outputs the electric signal to the processing circuitry 45 is also included in the example of the input interface 43. Furthermore, the input interface 43 may be provided on the gantry 10. In addition, the input interface 43 may be configured by a tablet terminal or the like capable of wirelessly communicating with the main body of the console 40.

The communication interface 44 includes a network interface card (NIC) or the like for communicating various data with an external device such as a workstation, a picture archiving and communication system (PACS), a radiology information system (RIS), or a hospital information system (HIS) via a network.

The processing circuitry 45 controls the entire operation of the X-ray computed tomography apparatus 1 according to the electric signal of the input operation output from the input interface 43. The processing circuitry 45 includes a processor such as a CPU and a memory such as a ROM and a RAM as hardware resources. The processing circuitry 45 implements various functions by a processor that executes a program expanded in a memory. The various functions are not limited to being implemented by a single processing circuitry. A processing circuitry may be configured by combining a plurality of independent processors, and each processor may execute a program to implement various functions.

Figure 2:
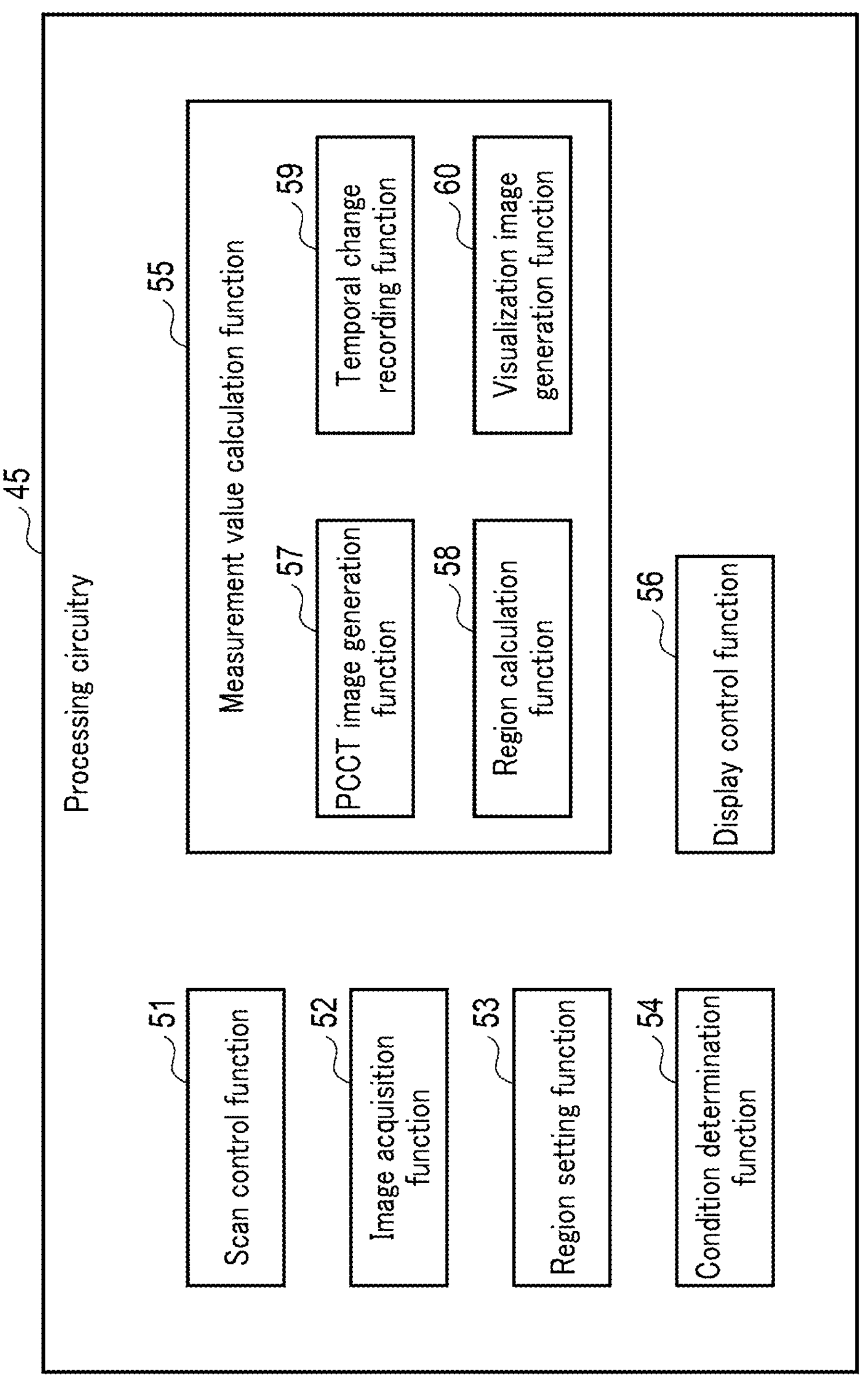
FIG. 2 is a diagram showing a functional configuration example of a processing circuitry shown in FIG. 1.

FIG. 2 is a diagram showing a functional configuration example of the processing circuitry 45. As shown in FIG. 2, the processing circuitry 45 implements a scan control function 51, an image acquisition function 52, a region setting function 53, a condition determination function 54, a measurement value calculation function 55, and a display control function 56.

In the scan control function 51, the processing circuitry 45 controls the gantry 10 to perform the PCCT scan on the subject P. With the PCCT scan performed, the data acquisition system 18 collects count data for each of the plurality of energy bins. As an example, the processing circuitry 45 controls the gantry 10 according to the scan condition determined by the condition determination function 54, and executes the PCCT scan, which is the second scan, on the subject P.

A region of interest present on the subject P is included in a first image. In the image acquisition function 52, the processing circuitry 45 acquires the first image collected by a first scan of the subject P. The first scan means a scan performed before the treatment of interest (hereinafter, subject treatment) among the treatments for the subject P. The first scan is not limited to the PCCT scan that can be performed by the X-ray computed tomography apparatus 1, and may be a PCCT scan and/or integrated CT scan that can be performed by another X-ray computed tomography apparatus, a volume CT scan that can be performed by an X-ray diagnostic apparatus, magnetic resonance imaging that can be performed by a magnetic resonance imaging apparatus, an ultrasonic scan that can be performed by an ultrasonic diagnostic apparatus, or positron emission tomography (PET) imaging or single photo emission CT (SPECT) imaging that can be performed by nuclear medicine diagnostic apparatus. The first image means a medical image generated based on raw data collected by the first scan.

In the region setting function 53, the processing circuitry 45 sets the specific region including the region of interest with respect to the first image acquired by the image acquisition function 52. The region of interest means a lesion site or tissue region to be followed up. The specific region means an image region that matches the region of interest or an image region obtained by adding a margin to the region of interest. The specific region can be set manually or automatically.

In the condition determination function 54, the processing circuitry 45 determines the scan condition of the PCCT scan, which is the second scan, based on the specific region set by the region setting function 53. The second scan is a PCCT scan performed by the X-ray computed tomography apparatus 1. The scan conditions include an X-ray dose and/or energy bin that matches the image quality standards for the region of interest. The processing circuitry 45 may further determine the tube voltage, the X-ray irradiation range in the rotation axis direction of the gantry 10, and/or the X-ray irradiation range in the fan angular direction of the X-ray as the scan condition.

In the measurement value calculation function 55, the processing circuitry 45 calculates the measurement values of the region of interest and/or the temporal change of the measurement values based on the count data collected by the data acquisition system 18 in the second scan. The processing circuitry 45 calculates, as measurement values, characteristic values for evaluating X-ray energy characteristics with respect to the region of interest, a three-dimensional region of the region of interest, and/or dimensions of the three-dimensional region.

In the display control function 56, the processing circuitry 45 displays various types of information on the display 42. As an example, the processing circuitry 45 displays the first image acquired by the image acquisition function 52, the specific region obtained by the region setting function 53, the scan condition obtained by the condition determination function 54, the measurement values obtained by the measurement value calculation function 55, and the like.

As shown in FIG. 2, the measurement value calculation function 55 specifically includes a PCCT image generation function 57, a region calculation function 58, a temporal change recording function 59, and a visualization image generation function 60.

In the PCCT image generation function 57, the processing circuitry 45 generates the PCCT image representing the spatial distribution of the characteristic value for evaluating the X-ray energy characteristics of each pixel based on the count data output from the data acquisition system 18. As the PCCT image, a count image representing a spatial distribution of CT values reconstructed based on count data of a specific energy bin, a basis material image representing a spatial distribution of density values of the basis material, a virtual monochromatic image representing a spatial distribution of CT values based on an X-ray attenuation coefficient at one X-ray energy, a material map representing a spatial distribution of CT values of the basis material, a K-edge image which is a count image based on an energy bin to which a K-edge of a substance of interest belongs, an effective atomic number image representing a spatial distribution of effective atomic numbers, an electron density image representing a spatial distribution of electron densities, and the like can be generated. The pixel value of the PCCT image such as the CT value, the density value, the effective atomic number, and the electron density is an example of the measurement values. For example, the processing circuitry 45 generates a second image that is a PCCT image representing the spatial distribution of the characteristic values regarding the region of interest based on the count data collected by the data acquisition system 18 in the second scan.

Here, the first image and/or the second image can be applied to both a two-dimensional image related to one slice or slab and a three-dimensional image related to one volume. Note that a two-dimensional image means image data including a plurality of pixels (pixels) arranged in a two-dimensional space, and a three-dimensional image means image data including a plurality of pixels (voxels) arranged in a three-dimensional space. Hereinafter, it is assumed that the first image and the second image are three-dimensional images.

In the region calculation function 58, the processing circuitry 45 calculates a three-dimensional region of the region of interest and/or the dimensions of the three-dimensional region based on the count data collected by the data acquisition system 18 in the second scan. For example, the processing circuitry 45 calculates a three-dimensional region of the region of interest based on the second image. In addition, the processing circuitry 45 may calculate the dimensions of the three-dimensional region. As the dimensions, it is sufficient that the diameter, volume, and the like of the three-dimensional region are used. The three-dimensional region and the dimensions of the three-dimensional region are examples of measurement values of the region of interest.

In the temporal change recording function 59, the processing circuitry 45 records the temporal change of the measurement values. For example, the processing circuitry 45 records a change from measurement values related to the first scan to measurement values related to the second scan as a temporal change.

In the visualization image generation function 60, the processing circuitry 45 generates a visualized image based on the first image acquired by the image acquisition function 52, the second image generated by the PCCT image generation function 57, the three-dimensional region calculated by the region calculation function 58 and/or the dimensions of the three-dimensional region, the temporal change recorded by the temporal change recording function 59, and the like.

The visualized image according to the present embodiment means image data displayed on the display 42. The processing circuitry 45 generates a visualized image for display by performing any visualization processing on an original image such as the first image and the second image. As the visualization processing, conversion processing from a three-dimensional image to a two-dimensional image, such as pixel value projection, multi-planar reconstruction (MPR), volume rendering, or surface rendering, can be used. Furthermore, the processing circuitry 45 can also perform synthesis processing or the like of a plurality of three-dimensional images or two-dimensional images. For example, the processing circuitry 45 generates a composite image of the first image and the second image. More specifically, the processing circuitry 45 generates a composite image in which the second image region corresponding to the first image region of the second image is fitted into or superimposed on the first image region with respect to the region of interest of the first image. Note that, in the present embodiment, in order to avoid complication of description, the images before and after the visualization processing are not particularly distinguished and referred to unless particularly necessary.

Hereinafter, a process example of the CT inspection by the X-ray computed tomography apparatus 1 will be described. In the following description, follow-up imaging of a tumor will be described as a clinical example. That is, it is assumed that the region of interest is a tumor such as cancer which is a lesion, and the subject treatment is radiation treatment or chemical treatment for the tumor. The first scan is assumed to be a PCCT scan performed by the X-ray computed tomography apparatus 1, and the first image is assumed to be a PCCT image based on count data collected by the PCCT scan. In the first scan, it is assumed that the subject is scanned under injection of a contrast medium for imaging a tumor.

Figure 3:
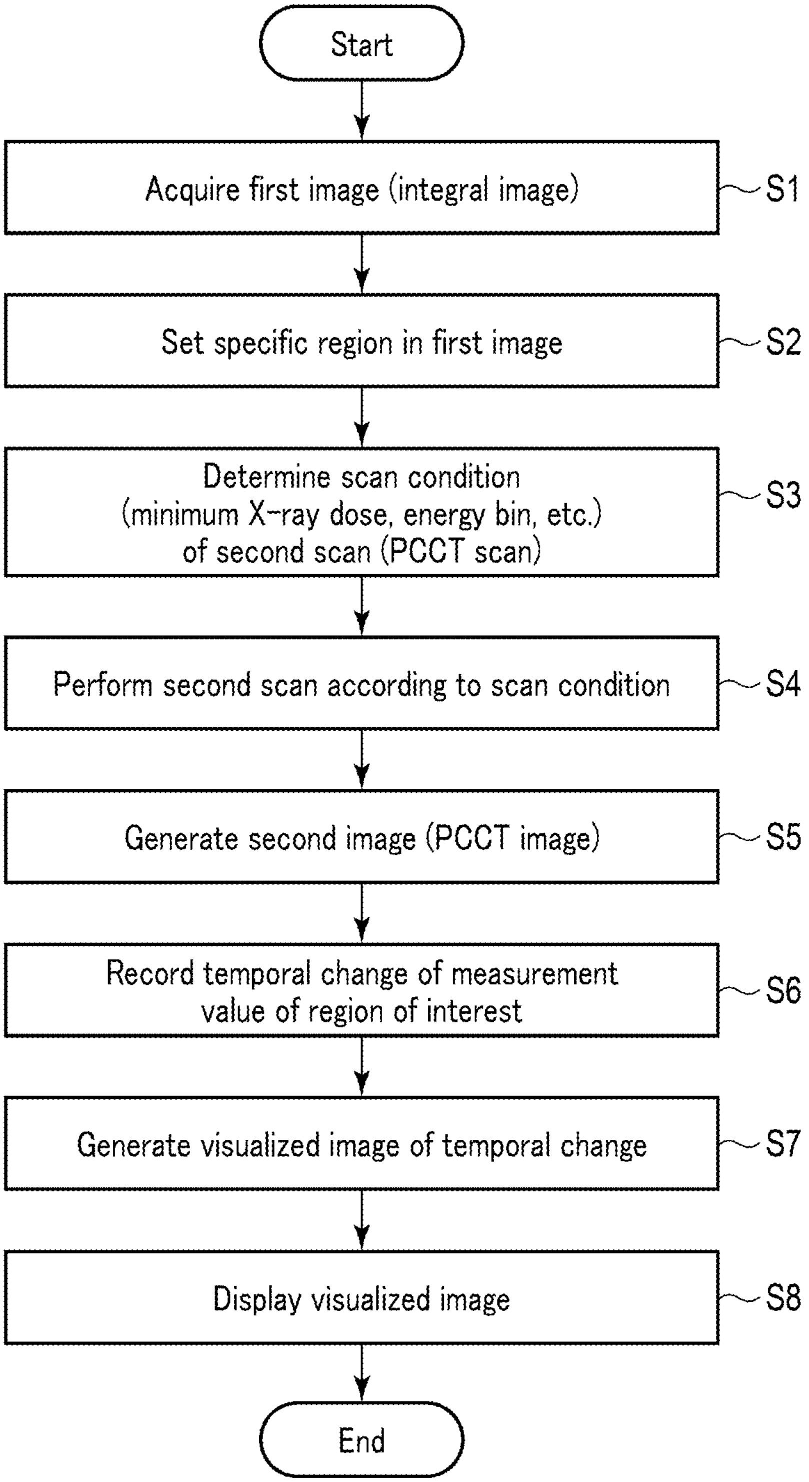
FIG. 3 is a view showing a process procedure of follow-up imaging by the X-ray computed tomography apparatus.

FIG. 3 is a view showing a process procedure of follow-up imaging by the X-ray computed tomography apparatus 1. The process shown in FIG. 3 is started at the time of performing the subject treatment or at the start of the inspection of the follow-up imaging after a lapse of a certain period of time from the performance of the subject treatment. It is assumed that the first image related to the subject P is obtained before the subject treatment and stored in the memory 41. In the first scan, the processing circuitry 45 implements the scan control function 51 to perform the PCCT scan as the first scan. By the first scan, the inspection region including the tumor present in the subject P is PCCT scanned. The first scan collects count data related to a plurality of energy bins. The scan condition for the first scan is not particularly limited. Then, the processing circuitry 45 reconstructs the PCCT image, which is the first image, based on the count data related to the plurality of energy bins. The type of the first image is not particularly limited, but as an example, it is assumed that the first image is an integral image reconstructed by applying a reconstruction algorithm such as filtered back projection (FBP) to integral data of count data of all energy bins among a plurality of energy bins.

As shown in FIG. 3, the processing circuitry 45 acquires the first image by implementing the image acquisition function 52 (step S1). In step S1, the processing circuitry 45 may acquire the first image from the memory 41 that stores the first image in advance. Note that the processing circuitry 45 may acquire the first image from a PACS or another X-ray computed tomography apparatus via the communication interface 44 or the like.

Once step S1 is performed, the processing circuitry 45 sets the specific region in the first image acquired in step S1 by implementing the region setting function 53 (step S2). In step S2, the processing circuitry 45 displays the first image on the display 42 by implementing the display control function 56 in order to set the specific region. A user designates the position of the specific region via the input interface 43 with respect to the first image displayed on the display 42. The processing circuitry 45 sets the specific region at the designated position.

Figure 4:
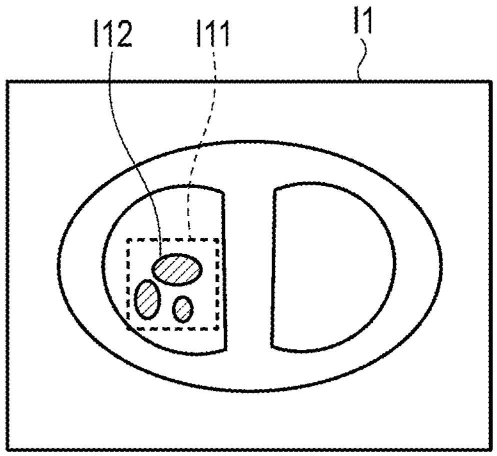
FIG. 4 is a view showing an example of a first image displayed in step S2.

FIG. 4 is a view showing an example of a first image I1 displayed in step S2. As an example, the first image I1 shown in FIG. 4 is assumed to be an axial cross-sectional image based on an integral image of the chest. As shown in FIG. 4, the first image I1 includes a tumor region I12 which is a region of interest. The contrast of the tumor region I12 is enhanced by the contrast medium. The user observes the first image I1 to confirm the position, size, type, and the like of the tumor region I12. Then, the user designates the position of a specific region I11 via the input interface 43. The specific region I11 means a region where the user desires follow-up imaging. Typically, the position of the specific region I11 is designated so as to surround the tumor region 112 to be treated. If the position is designated, the processing circuitry 45 sets the specific region I11 to the designated position. The position of the specific region I11 is stored in the memory 41.

If step S2 is performed, the processing circuitry 45 determines the scan condition for the second scan by implementing the condition determination function 54 (step S3). The second scan means a PCCT scan for follow-up imaging. In step S3, the processing circuitry 45 determines a minimum X-ray dose and an energy bin as the scan condition. Note that scan conditions used in normal PCCT scanning, such as tube voltage, detector resolution, and gantry rotation speed, may be further determined. Furthermore, the processing circuitry 45 may determine an image generation purpose including information such as the type of the PCCT image generated in the second scan as the scan condition. The type of the PCCT image generated in the second scan is not particularly limited, but is assumed to be a k-edge image. These scan conditions may be determined by any method. The determined scan conditions are stored in the memory 41.

Here, the determination of the minimum X-ray dose will be described. The lowest X-ray dose means the lowest dose among the X-ray doses that conform to the image quality standards of the tumor region as the region of interest. In other words, the minimum X-ray dose means the minimum X-ray dose that can determine the temporal change of the tumor region. The temporal change means a change in the shape, characteristics, and the like of the tumor region from the time of the first scan to the time of the second scan. The tube current value in the second scan is determined depending on the lowest X-ray dose.

Figure 5:
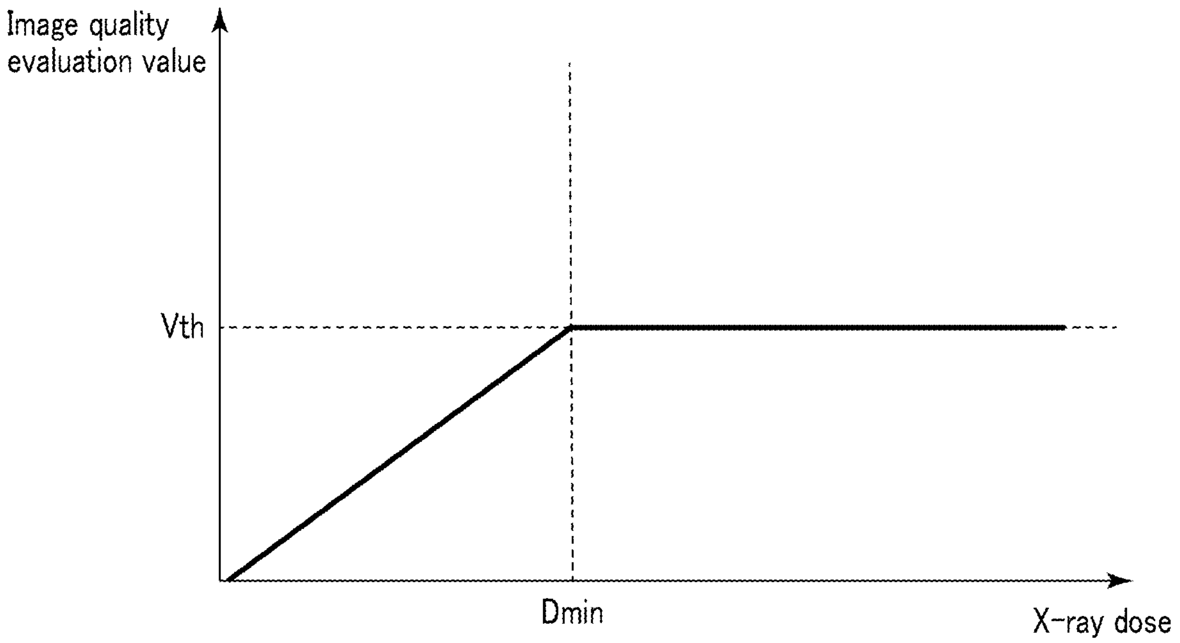
FIG. 5 is a diagram showing an example of a determination process of a minimum X-ray dose Dmin.

FIG. 5 is a diagram showing an example of a determination process of the minimum X-ray dose Dmin. The vertical axis of the graph shown in FIG. 5 represents an image quality evaluation value, and the horizontal axis represents the X-ray dose. The graph shown in FIG. 5 shows the relationship between the image quality evaluation value and the X-ray dose. As the image quality evaluation value, it is sufficient that an index value for evaluating image quality such as a signal-to-noise ratio (SN ratio) or a contrast-to-noise ratio (CNR) is used. The X-ray dose means the dose of the X-ray emitted from the X-ray tube 11 in the second scan. As shown in FIG. 5, the image quality evaluation value varies in a case where the X-ray dose is low, but tends to be stabilized at a substantially constant value in a case where the X-ray dose is equal to or greater than a certain value.

The image quality standards mean reaching the reference value Vth of the image quality evaluation value expected to be able to recognize the temporal change of the tumor region. Specifically, the reference value Vth is set to the image quality evaluation value capable of recognizing the temporal change of the tumor region. The reference value Vth may be empirically determined, may be determined by prediction calculation, or may be determined as an arbitrary value by the user. Typically, the reference value Vth is set to a plateau value of the image quality evaluation value, but may be set to any value. As an example, the processing circuitry 45 uses the prediction calculation of the second scan based on the probability distribution of the occurrence probability of the X-ray photons to determine the minimum X-ray dose satisfying the image quality standards. Specifically, since the occurrence probability of the X-ray photon follows the Poisson distribution, the transition of the image quality evaluation value such as the SN ratio when the X-ray dose is increased according to the Poisson distribution is predicted and calculated. The processing circuitry 45 determines the X-ray dose when the image quality evaluation value reaches the reference value Vth as the minimum X-ray dose Dmin. Here, as the image quality evaluation value, an image quality evaluation value limited to a specific region or a region of interest may be calculated. In addition, the image quality evaluation value can also depend on other scan conditions other than the X-ray dose, for example, an energy bin, a tube voltage, a scan range, and the like. It is assumed that these scan conditions are set to values that can be used in the second scan.

Here, the determination of the minimum X-ray dose Dmin when the tumor region is observed in the image will be described. As the image, it is assumed that a k-edge image based on the count data of an energy bin adjacent to an energy bin to which the k-edge of the contrast agent belongs and the count data of all energy bins is used. In this case, the processing circuitry 45 determines the minimum required X-ray dose for detecting the k-edge of the contrast agent that accumulates in the tumor. Specifically, the processing circuitry 45 predicts and calculates the transition of the image quality evaluation value of the specific region in the k-edge image when the X-ray dose is increased according to the Poisson distribution. Then, the processing circuitry 45 may determine the X-ray dose when the image quality evaluation value reaches the reference value Vth as the minimum X-ray dose Dmin.

In the above process, the k-edge image is exemplified as the image, but the image is not limited thereto. For example, a count image based on count data of an energy bin to which the k-edge of the contrast agent accumulating in the tumor region belongs may be used. The calculation target of the image quality evaluation value is not limited to the specific region, and may be the tumor region.

The method for determining the minimum X-ray dose is not limited only to the above method. As an example, the processing circuitry 45 may determine the lowest X-ray dose based on the image quality evaluation value of the specific region in the first image using the AEC technique. Specifically, the processing circuitry 45 determines the minimum X-ray dose based on the body thickness of the subject P and the image quality evaluation value. The relationship between the combination of the body thickness and the image quality evaluation value and the minimum X-ray dose is recorded in advance in a lookup table (LUT). The body thickness may be calculated by image processing based on a scanogram image or an optical image captured by an optical camera.

The determination of the energy bins will now be described. The processing circuitry 45 determines an energy bin for detecting the k-edge of the contrast agent accumulating in the tumor. More particularly, as energy bins, the number of energy bins and the energy range for each energy bin are determined.

Figure 6:
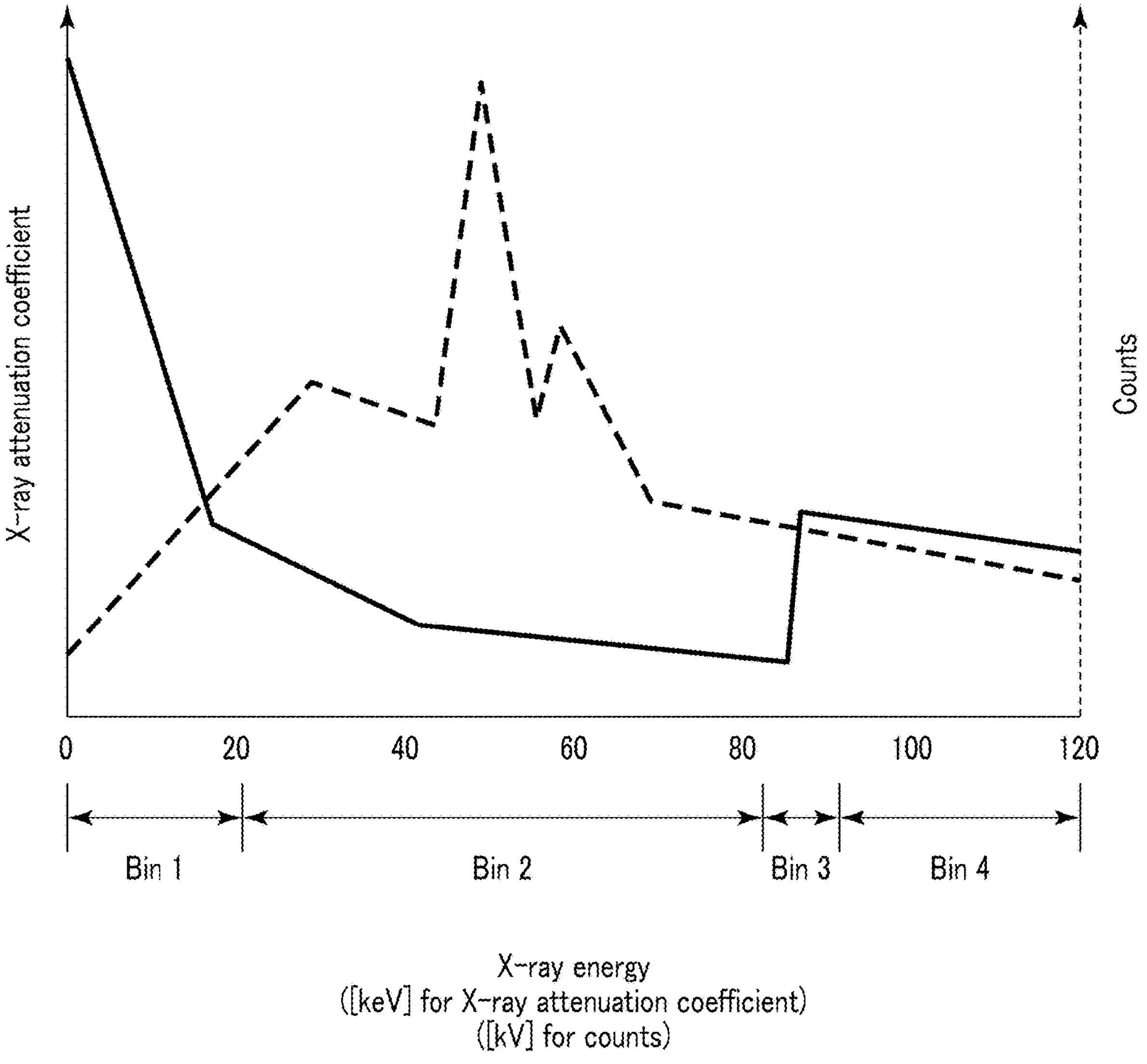
FIG. 6 is a diagram showing an example of an energy bin determination process.

FIG. 6 is a diagram showing an example of an energy bin determination process. The vertical axis on the left side of the graph shown in FIG. 6 represents an X-ray attenuation coefficient, the vertical axis on the right side represents the number of the count of X-ray photons, and the horizontal axis represents X-ray energy. The unit of the X-ray energy with respect to the X-ray attenuation coefficient is keV, and the unit of the X-ray energy with respect to the number of the count is kV. The broken line in FIG. 6 represents a typical energy spectrum of the X-rays emitted from the X-ray tube 11, and the solid line represents the X-ray attenuation coefficient of the contrast agent used for the second scan. As indicated by the solid line in FIG. 6, the contrast agent used for the second scan has a k-edge in the vicinity of 80 keV.

The number of energy bins to be set and the energy range of each energy bin can be arbitrarily set. As an example, it is assumed that the number of set energy bins is four. The first energy bin (bin 1) is set to 0 to 20 keV, which corresponds to the noise range. The third energy bin (bin 3) is set to 81 to 83 keV, which corresponds to a narrow energy range including a k-edge. The second energy bin (bin 2) is set between the first energy bin and the third energy bin and the fourth energy bin (bin 4) is set between the third energy bin and the energy value corresponding to the tube voltage value (120 keV).

Once step S3 is performed, the processing circuitry 45 implements the scan control function 51 to perform the second scan according to the scan condition determined in step S3 (step S4). The second scan is performed at the timing when the contrast agent accumulates in the tumor present in the subject P. The start timing of the second scan may be determined by a monitoring scan or may be arbitrarily determined in consideration of an empirical rule in the elapsed time from the start of injection of the contrast agent. Note that the processing circuitry 45 sets the number of energy thresholds and/or the value of the energy threshold of the data acquisition system 18 according to the number of energy bins and/or the energy range determined in step S3 before performing the second scan. At the time of PCCT scan, the processing circuitry 45 performs feedback control on the X-ray high-voltage device 14 based on the tube voltage value determined in step S3 and the tube current value corresponding to the minimum X-ray dose. In the PCCT scan, the data acquisition system 18 acquires count data for a plurality of energy bins. The collected count data is transmitted to the console 40.

Once step S4 is performed, the processing circuitry 45 generates the second image by implementing the PCCT image generation function 57 (step S5). In step S5, the processing circuitry 45 reconstructs the PCCT image as the second image based on the count data collected in step S4. The type of the PCCT image is not particularly limited, but it is assumed that a k-edge image is generated as described above.

Once step S5 is performed, the processing circuitry 45 records the temporal change of the measurement values of the tumor region as the region of interest by implementing the temporal change recording function 59 (step S6). The measurement values may be the characteristic value described in the above embodiment or a spatial distribution of the characteristic value, may be a tumor region as a three-dimensional region, or may be the dimensions of the tumor region. In step S5, as an example, the processing circuitry 45 records a change from the measurement values at the time of the first scan to the measurement values at the time of the second scan as a temporal change. Specifically, the measurement values of the tumor region included in the first image may be used as the measurement values at the time of the first scan. Specifically, the measurement values of the tumor region included in the second image may be used as the measurement values at the time of the second scan.

Once step S5 is performed, the processing circuitry 45 generates a visualized image of temporal change calculated in step S5 by implementing the visualization image generation function 60 (step S7). Once step S6 is performed, the processing circuitry 45 displays the visualized image generated in step S6 on the display 42 by implementing the display control function 56 (step S8). Here, steps S5, S6, and S7 will be specifically described. In the following description, the measurement values are assumed to be the dimensions of the three-dimensional region of the tumor region as the region of interest.

In step S5, the processing circuitry 45 first calculates the dimensions of the tumor region as the region of interest by implementing the region calculation function 58. Specifically, the processing circuitry 45 extracts a tumor region from the second image and calculates dimensions of the extracted tumor region. As the dimensions, the diameter, area, and volume of the tumor region may be calculated. Next, by implementing the temporal change recording function 59, the processing circuitry 45 records the temporal change from the dimensions of the tumor region at the time of the first scan to the dimensions of the tumor region at the time of the second scan. It is assumed that the dimensions of the tumor region at the time of the first scan are calculated in advance by the processing circuitry 45. Then, the processing circuitry 45 generates a visualized image representing the calculated temporal change, and displays the generated visualized image on the display 42.

Figure 7:
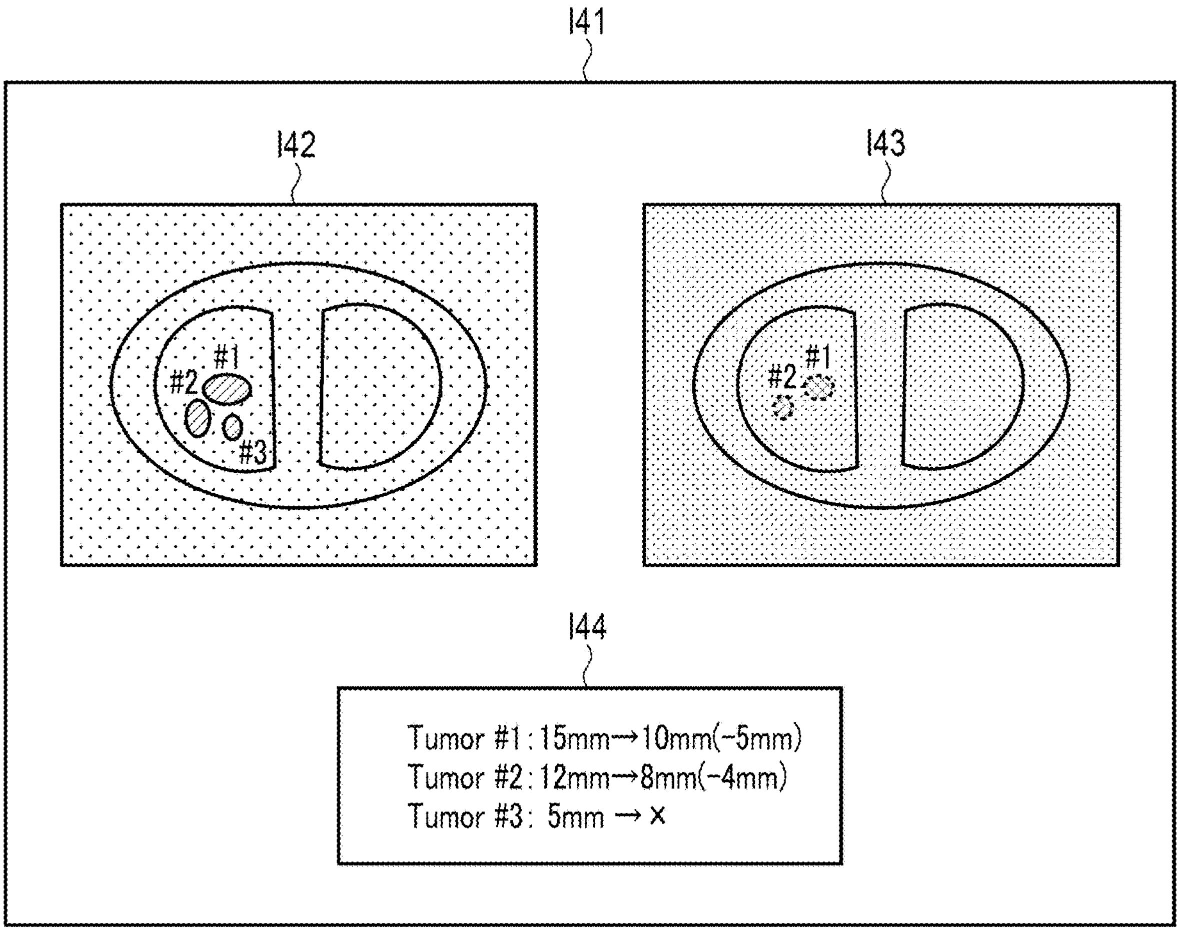
FIG. 7 is a diagram showing an example of a visualized image representing a temporal change of measurement values.

FIG. 7 is a diagram showing an example of a visualized image 141 representing a temporal change. As shown in FIG. 7, the visualized image 141 includes a first image 142, a second image 143, and a display field 144. The processing circuitry 45 may display the first image 142 and the second image 143 side by side. By displaying the first image 142 and the second image 143 side by side, the user can confirm the morphological temporal change of the tumor region. Note that an annotation indicating a code for identifying each tumor region, such as "#1", "#2", and "#3", may be added to the first image 142 and the second image 143. The same reference numeral is assigned to the same tumor region.

The display field 144 displays the time change from the dimensions of the tumor region at the time of the first scan to the dimensions of the tumor region at the time of the second scan recorded by the temporal change recording function 59. As the temporal change, a dimensional transition and a difference value for each tumor region, such as "Tumor #1:15 mm→10 mm (−5 mm), Tumor #2:12 mm→8 mm (−4 mm)", are displayed. If the tumor disappears at the time of the second scan as in the case of the tumor #3, that is, if the tumor #3 does not exist in the second image 143, it is preferable to display that the tumor region does not exist at the time of the second scan, as in "Tumor #3:5 mm→x".

Since the first scan for the first image 142 is performed with an X-ray dose that takes into account the image quality of the entire image, the image quality of the entire image of the first image 142 is good, but the image quality is not specialized for the tumor region. Since the second scan is performed at the lowest X-ray dose at which the k-edge of the contrast agent accumulating in the tumor can be detected, it is assumed that the image quality of the tumor region of the second image 143 is appropriate although the dose is low. Therefore, it is expected that the temporal change of the dimensions of the tumor region is also obtained with appropriate accuracy. Since the temporal change of the measurement values, which is information useful for follow-up observation of the tumor region, is displayed, follow-up observation can be easily and accurately performed.

Thus, the processing related to the follow-up imaging shown in FIG. 3 ends.

In the above embodiment, the temporal change of the dimensions has been described as a specific example of the time change, but the present embodiment is not limited thereto. For example, an image representing the spatial distribution of the difference value between the characteristic value of the X-ray energy at the time of the first scan and the characteristic value of the X-ray energy at the time of the second scan may be recorded and displayed as the temporal change. As the characteristic value in this case, an effective atomic number, an electron density, and the like are useful. The difference value between the effective atomic number and the electron density represents a degeneration of the tissue existing in the pixel to which the difference value is allocated. By observing the spatial distribution of the difference values, the user can confirm the anatomical region where the degeneration of the tissue has occurred.

The degeneration of the tissue can also be observed as a change in an energy spectrum (frequency distribution of count values across a plurality of energy bins) that can be measured by PCCT. The processing circuitry 45 may determine the degeneration of the tissue based on the difference between the count data at the time of the first scan and the count data at the time of the second scan, and display the determination result as the temporal change of the measurement values.

Note that, in the present embodiment, various elements can be added, deleted, and/or changed without departing from the gist of the invention.

First Modification

The processing circuitry 45 according to the above embodiment records the temporal change of the measurement values of the region of interest. It is assumed that the processing circuitry 45 according to the first modification calculates a PCCT image, which is a spatial distribution of the characteristic values of the X-ray energy characteristics, as the measurement values of the region of interest. Hereinafter, processing related to follow-up imaging according to the first modification will be described with reference to FIG. 3. Note that steps S1 to S5 are the same as those in the above embodiment, and thus description thereof is omitted.

Once step S5 is performed, the processing circuitry 45 generates a composite image of the first image acquired in step S1 and the second image generated in step S5 by implementing the visualization image generation function 60 (step S6). Here, steps S5 and S6 according to the first modification will be specifically described.

Figure 8:
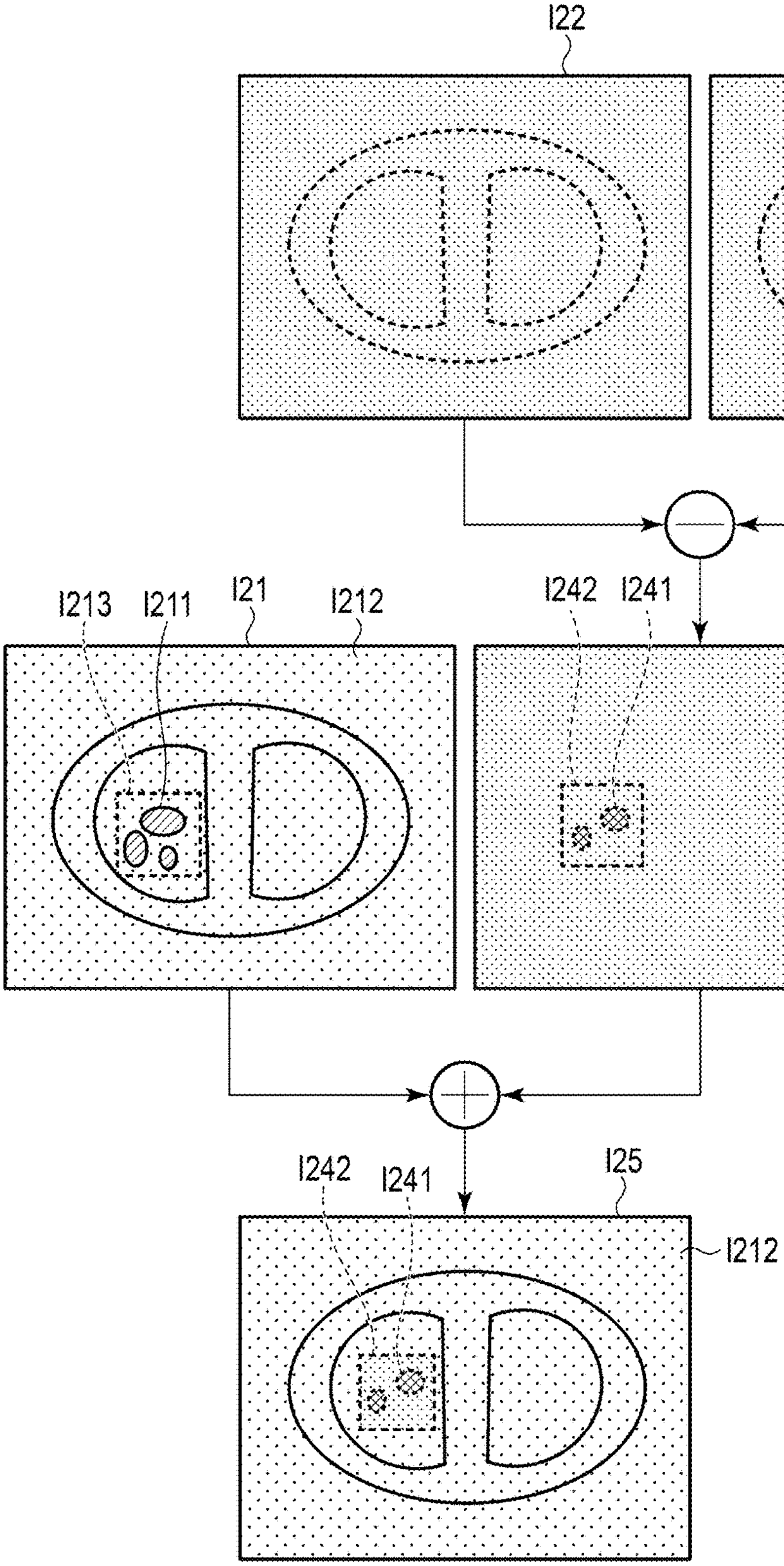
FIG. 8 is a view schematically showing process procedures of steps S5 and S6 according to a first modification.

FIG. 8 is a view schematically showing process procedures of steps S5 and S6 according to the first modification. As shown in FIG. 8, first image I21 is acquired in step S1. It is assumed that the first image I21 includes three tumor regions I211. Since the first scan for the first image 121 is performed with an X-ray dose that takes into account the image quality of the entire image, the image quality of the entire image of the first image I21 is good, but the image quality is not specialized for the tumor region I211.

As shown in FIG. 8, the processing circuitry 45 generates a k-edge image 124 that is an example of the second image. A method of generating the k-edge image 124 is as follows. The number of energy bins and the energy range are set as shown in FIG. 6. First, the processing circuitry 45 individually reconstructs a first count image 122 based on the count data of the second and fourth energy bins collected in the second scan and a second count image 123 based on the count data of the second, third and fourth energy bins collected in the second scan. As described above, the third energy bin is the energy bin to which the k-edge of the contrast agent injected into the subject P belongs. Therefore, it is assumed that a tumor region is not included in the first count image 122, and a tumor region 1231 is included in the second count image 123. Note that it is assumed that the tumor has disappeared or been reduced by the subject treatment performed before the second scan, and the second count image 123 includes two tumor regions I231. As described above, since the second scan is performed at the minimum X-ray dose at which the k-edge of the tumor can be detected, it is assumed that the image quality of the first count image 122 and the second count image 123 is worse than that of the first image 121.

Next, as shown in FIG. 8, the processing circuitry 45 generates a k-edge image 124 by subtracting the first count image 122 from the second count image I23. In the k-edge image 124, a tumor region 1241 in which contrast is enhanced by a contrast agent is included. It is assumed that a region other than the tumor region 1241 is eliminated or imaged with low contrast.

As shown in FIG. 8, the processing circuitry 45 generates a composite image 125 based on the first image I21 and the k-edge image 124 such that an image region (hereinafter, the peripheral region) 1212 other than the specific region 1213 in the first image 121 and the tumor region 1241 in the k-edge image 124 are included. A method of generating the composite image 125 is not particularly limited.

As an example, the processing circuitry 45 generates the composite image 125 by fitting an image region (hereinafter, the corresponding region) 1242 corresponding to the specific region 1213 in the k-edge image I24 into the specific region 1213 in the first image I21. Specifically, first, the processing circuitry 45 reads the position of the specific region 1213 in the k-edge image 124 from the memory 41, and specifies an image region corresponding to the read position as the corresponding region 1242. Note that the position of the specific region 1213 is specified in advance in step S2 and stored in the memory 41. Next, the processing circuitry 45 cuts out the corresponding region 1242 and replaces the specific region 1213 of the first image I21 with the cut-out corresponding region 1242. As a result, the composite image 125 including the peripheral region I212 and the corresponding region 1242 is generated. Alternatively, the processing circuitry 45 may generate the composite image 125 by superimposing the cut-out corresponding region 1242 on the specific region 1213.

The method for generating the composite image I25 is not limited to the above method. For example, in the above embodiment, the processing circuitry 45 cuts out the specific region to be fitted or superimposed from the k-edge image. However, the processing circuitry 45 may cut out the specific region from the PCCT image including the specific region such as the second count image I23 shown in FIG. 8. Alternatively, the processing circuitry 45 may reconstruct only the specific region data based on the count data relating to the plurality of energy bins.

Once step S6 according to the first modification is performed, the processing circuitry 45 displays the combined image generated in step S6 by implementing the display control function 56 (step S7). In step S7, the processing circuitry 45 displays the composite image on the display 42. The user performs follow-up observation or the like of a tumor region or the like included in the composite image displayed on the display 42. As described above, the peripheral region I212 in the composite image 125 shown in FIG. 8 is derived from the first image 121 and thus has a relatively high image quality, and the corresponding region I242 is derived from the count images 122 and 123 obtained at the lowest X-ray dose capable of detecting the k edge of the contrast agent and thus is expected to have a low dose and an appropriate image quality. By observing the tumor region 1241 using such a composite image I25, it is possible to perform follow-up with a low dose and appropriate image quality.

Second Modification

It is assumed that the processing circuitry 45 according to the first modification calculates a PCCT image, which is a spatial distribution of the characteristic values of the X-ray energy characteristics, as the measurement values of the region of interest. It is assumed that the processing circuitry 45 according to a second modification calculates the three-dimensional region of the tumor region as the measurement values of the region of interest.

Hereinafter, processing related to follow-up imaging according to the second modification will be described with reference to FIG. 3. Note that steps S1 to S5 are the same as those in the above embodiment, and thus description thereof is omitted.

Once step S5 is performed, the processing circuitry 45 calculates the three-dimensional region of the tumor region as the region of interest by implementing the region calculation function 58 (step S6). Once step S6 is performed, the processing circuitry 45 generates a composite image of the first image acquired in step S1 and the three-dimensional region generated in step S6 by implementing the visualization image generation function 60 (step S7). Here, steps S6 and S7 according to the second modification will be specifically described.

Figure 9:
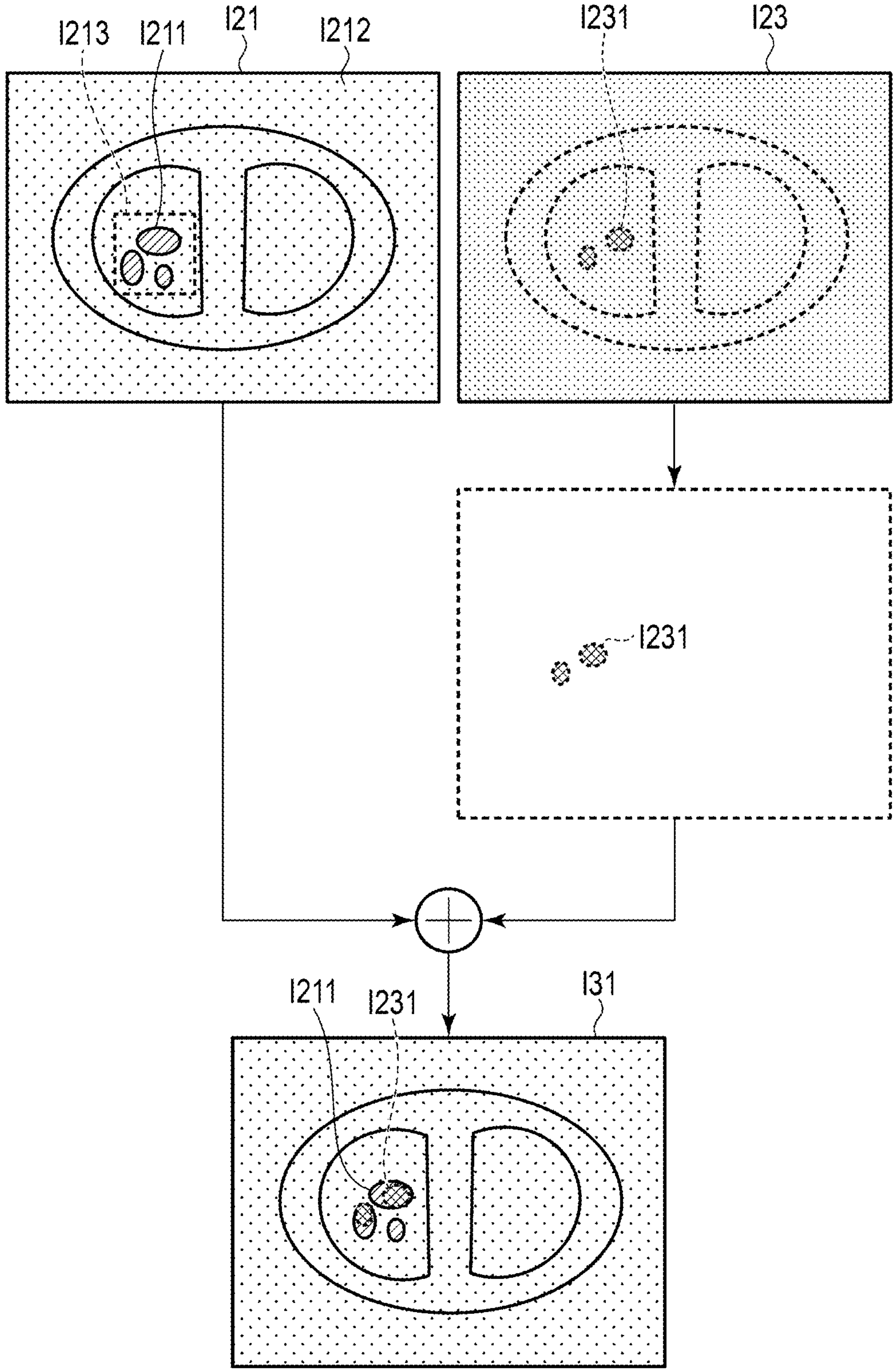
FIG. 9 is a view schematically showing process procedures of steps S6 and S7 according to a second modification.

FIG. 9 is a view schematically showing process procedures of steps S6 and S7 according to the second modification. As shown in FIG. 9, the first image I21 is acquired in step S1. The processing circuitry 45 reconstructs a count image 123 based on the count data of the second, third and fourth energy bins collected in the second scan. As described above, the third energy bin is the energy bin to which the k-edge of the contrast agent injected into the subject P belongs. The tumor region I231 is included in the count image 123.

Next, the processing circuitry 45 aligns the first image 121 and the count image 123. Next, the processing circuitry 45 extracts the tumor region 1231 from the count image 123. The tumor region 1231 is an example of the three-dimensional region. As an extraction method, any method such as threshold processing, a region growth method, machine learning, and extraction of a user-designated region may be used. Then, as shown in FIG. 9, the processing circuitry 45 aligns and superimposes the extracted tumor region 1231 on the first image I21. As a result, the tumor region 1231 derived from the count image 123 after the subject treatment is superimposed on the tumor region 1211 derived from the first image 121 before the subject treatment. The first image I21 on which the tumor region 1231 is superimposed is a composite image 131. In order to make the tumor region I211 visible, the processing circuitry 45 may perform visualization processing on the tumor region 1231 and then superimpose the processed tumor region 1231 on the first image 121. As an example, visualization processing may be performed such that the tumor region I231 is visually emphasized as compared with the tumor region I211. Specifically, setting of transparency, setting of a color value, molding of a region shape, and the like may be performed as the visualization processing.

Thereafter, the processing circuitry 45 displays the composite image on the display 42 (step S8). The user performs follow-up observation or the like of a tumor region or the like included in the composite image displayed on the display 42.

According to the second modification, since the tumor region at the time of the second scan is superimposed on the first image, it is possible to compare the tumor region at the time of the first scan and the tumor region at the time of the second scan on one image. In addition, it is also possible to enhance the visibility of the tumor region by performing visualization processing on the tumor region at the time of the second scan.

Third Modification

The processing circuitry 45 according to the above embodiment determines the minimum X-ray dose, the energy bin, and the like as the scan condition. The processing circuitry 45 according to the third modification may further determine the X-ray irradiation range in the rotation axis direction of the gantry 10, and/or the X-ray irradiation range in the fan angular direction of the X-ray.

Figure 10:
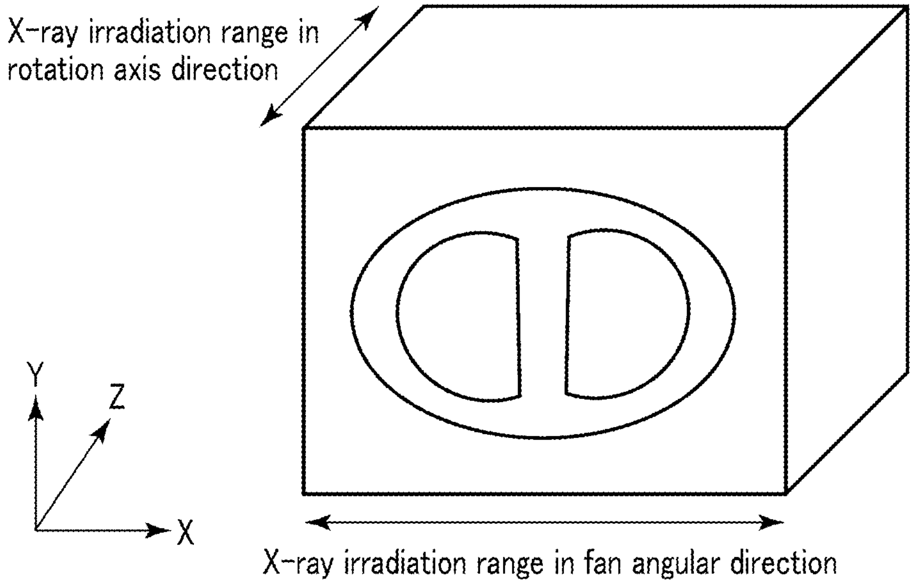
FIG. 10 is a view showing an X-ray irradiation range according to a third modification.

FIG. 10 is a view showing an X-ray irradiation range according to the third modification. As shown in FIG. 10, the X-ray irradiation range in the rotation axis Z direction means the X-ray irradiation range in the cone angle direction of the X-ray emitted from the X-ray tube 11 or the body axis direction of the subject P. The X-ray irradiation range in the fan angular direction of the X-ray emitted from the X-ray tube 11 means the rotation direction of the X-ray tube 11, the X-ray detector 12, the rotary frame 13, and the like about the rotation axis Z. By limiting the X-ray irradiation range in the rotation axis Z direction and/or the fan angular direction to a specific region, the exposure dose of the subject P can be reduced.

Conclusion

According to the above description, the X-ray computed tomography apparatus 1 according to the present embodiment includes the gantry 10 and the processing circuitry 45. The gantry 10 includes the X-ray tube 11 that generates an X-ray, the X-ray high-voltage device 14 that applies a high voltage to the X-ray tube 11, the X-ray detector 12 that detects the X-ray generated from the X-ray tube 11, and the data acquisition system 18 that collects count data of the X-ray detected by the X-ray detector 12 for each energy bin. A region of interest present on the subject P is included in a first image. The processing circuitry 45 acquires the first image collected by a first scan of the subject P. The processing circuitry 45 sets a specific region including the region of interest with respect to the first image. The processing circuitry 45 determines a scan condition of a photon counting CT scan which is a second scan based on the specific region, and the scan condition includes an X-ray dose and/or an energy bin conforming to the image quality standards of the region of interest. The processing circuitry 45 controls the gantry 10 according to the scan condition and executes the second scan on the subject P.

According to the above configuration, it is possible to perform follow-up imaging by the PCCT scan with an X-ray dose and/or energy bin conforming to the image quality standards of the region of interest. In this way, by setting the image quality standards specialized for the region of interest and performing the PCCT scan with the X-ray dose and/or the energy bin satisfying the standards, it is possible to secure the image quality of the image using the energy bin and to reduce the exposure dose of the subject P as compared with the scan taking into account the image quality of the entire image.

According to at least one embodiment described above, it is possible to reduce the exposure dose while securing the measurement information of the specific region in the PCCT scan.

The term "processor" used in the above description means, for example, a CPU, a GPU, or a circuit such as an application specific integrated circuit (ASIC) or a programmable logic device (for example, a simple programmable logic device (SPLD), a complex programmable logic device (CPLD), and a field programmable gate array (FPGA)). The processor implements a function by reading and executing a program stored in the storage circuit. Instead of storing the program in the storage circuit, the program may be directly incorporated in the circuit of the processor. In this case, the processor implements the function by reading and executing the program incorporated in the circuit. On the other hand, in a case where the processor is, for example, an ASIC, the function is directly incorporated as a logic circuit in a circuit of the processor instead of storing the program in the storage circuit. Note that each processor of the present embodiment is not limited to a case where each processor is configured as a single circuit, and a plurality of independent circuits may be combined and configured as one processor to implement the function. Furthermore, a plurality of components in FIGS. 1 and 2 may be integrated into one processor to implement the function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:

a gantry including an X-ray tube that generates an X-ray, a high-voltage device that applies a high voltage to the X-ray tube, an X-ray detector that detects the X-ray generated from the X-ray tube, and a data acquisition system that collects count data of the X-ray detected by the X-ray detector for each energy bin; and a processing circuitry, wherein the processing circuitry is configured to:

acquire a first image in which a region of interest present on a subject is included, the first image being collected by a first scan of the subject;

set a specific region including the region of interest with respect to the first image;

determine a scan condition for a photon counting CT scan as a second scan based on the specific region, the scan condition including an X-ray dose and/or an energy bin conforming to an image quality standard of the region of interest; and control the gantry according to the scan condition to execute the second scan on the subject.

2. The X-ray computed tomography apparatus according to claim 1, wherein the processing circuitry is configured to:

calculate a measurement value of the region of interest and/or a temporal change of the measurement value based on count data collected by the data acquisition system in the second scan; and display the measurement value and/or the temporal change on a display device.

3. The X-ray computed tomography apparatus according to claim 2, wherein the processing circuitry is configured to calculate, as the measurement value, characteristic values for evaluating X-ray energy characteristics with respect to the region of interest, a three-dimensional region of the region of interest, and/or dimensions of the three-dimensional region.

4. The X-ray computed tomography apparatus according to claim 3, wherein the processing circuitry is configured to:

generate a second image that is a photon counting CT image representing a spatial distribution of the characteristic values with respect to the region of interest based on the count data collected by the data acquisition system in the second scan; and display the second image.

5. The X-ray computed tomography apparatus according to claim 4, wherein the processing circuitry is configured to display a composite image in which an image region corresponding to the specific region of the second image is fitted into or superimposed on the specific region of the first image.

6. The X-ray computed tomography apparatus according to claim 3, wherein the measurement value is the three-dimensional region, and the processing circuitry is configured to display a composite image in which the three-dimensional region is superimposed on an image region with respect to the region of interest of the first image.

7. The X-ray computed tomography apparatus according to claim 2, wherein the processing circuitry is configured to record, as the temporal change, a change from the measurement value related to the first scan to the measurement value related to the second scan.

8. The X-ray computed tomography apparatus according to claim 1, wherein the image quality standard is that an image quality evaluation value exceeds a reference value, and the processing circuitry is configured to determine the X-ray dose using prediction calculation of the second scan based on a probability distribution of occurrence probability of X-ray photons.

9. The X-ray computed tomography apparatus according to claim 1, wherein the region of interest is a tumor, and the processing circuitry is configured to determine the minimum required X-ray dose to detect a k-edge of a contrast agent that accumulates in the tumor.

10. The X-ray computed tomography apparatus according to claim 1, wherein the image quality standard is that an image quality evaluation value exceeds a reference value, and the processing circuitry is configured to determine the X-ray dose based on an image quality evaluation value of the specific region in the first image.

11. The X-ray computed tomography apparatus according to claim 10, wherein the region of interest is a tumor, and the processing circuitry is configured to further determine, as the scan condition, an energy bin for detecting a k-edge of a contrast agent that accumulates in the tumor.

12. The X-ray computed tomography apparatus according to claim 1, wherein the processing circuitry is configured to further determine, as the scan condition, an X-ray irradiation range in a rotation axis direction of the gantry and/or an X-ray irradiation range in a fan angular direction of the X-ray.

13. The X-ray computed tomography apparatus according to claim 1, wherein the first image is an integral image collected by a PCCT scan.

* * * * *